United States Patent [19]
Claro

[11] Patent Number: 5,624,407
[45] Date of Patent: Apr. 29, 1997

[54] MEDICATION INJECTING DEVICE AND ACCESSORIES THEREFOR

[76] Inventor: Jorge A. R. Claro, R. Alfredo Whatley, 536 -Resende - RJ, Brazil

[21] Appl. No.: 343,532

[22] PCT Filed: Apr. 4, 1994

[86] PCT No.: PCT/BR94/00007

§ 371 Date: Feb. 2, 1995

§ 102(e) Date: Feb. 2, 1995

[87] PCT Pub. No.: WO94/22509

PCT Pub. Date: Oct. 13, 1994

[30] Foreign Application Priority Data

Mar. 31, 1993 [BR] Brazil ..................... 9301376

[51] Int. Cl.$^6$ ..................... A61M 5/178
[52] U.S. Cl. ..................... 604/216; 604/212
[58] Field of Search ............ 604/212, 214, 604/216, 217, 251, 408, 113, 114, 232, 187, 132, 133, 411, 405, 207, 131, 134, 177; 222/95, 96, 103

[56] References Cited

U.S. PATENT DOCUMENTS

| | | | |
|---|---|---|---|
| 1,222,814 | 4/1917 | Storz | 604/214 |
| 2,227,566 | 1/1941 | Angell | 604/114 |
| 2,911,972 | 11/1959 | Elinger | 604/216 |
| 4,294,250 | 10/1981 | Dennehey | 604/408 |
| 4,581,021 | 4/1986 | Landau et al. | 604/212 |
| 4,692,157 | 9/1987 | Landau et al. | 604/214 |
| 4,880,409 | 11/1989 | Winbald et al. | 604/73 |
| 5,328,477 | 7/1994 | Sitko | 604/134 |
| 5,368,569 | 11/1994 | Sanese | 604/113 |

FOREIGN PATENT DOCUMENTS

| | | | |
|---|---|---|---|
| 0278032 | 12/1965 | Australia | 604/217 |
| 0348682 | 6/1986 | European Pat. Off. | |

Primary Examiner—Corrine M. McDermott
Assistant Examiner—V. Alexander
Attorney, Agent, or Firm—Nath & Associates; Gary M. Nath

[57] ABSTRACT

The present invention is a device for the administration, in humans and animals of therapeutical or diagnostic fluids, with the device already containing the fluid for injection, ready for use, eliminating the need for glass vials, ampules and conventional syringes. The device is constituted by a plastic, flexible, neutral non-reacting pressure resistant, internally coated recipient, with a conical or cylindrical shape in an upper view, oval in transversal cut-off, containing at its tapered portion a heat sealed terminal with a fitting connection, tubular section, wing and reinforced by a pressure ring. For low injection volumes, the recipient is placed between plates, with a scale portion and injected volume indicator. For drip infusion, the recipient is hung up, and is equipped with a luer-lock terminal, a flow control valve, dropping chamber, tubing, needle, and air filter. For large volumes injection, the flexible recipient is installed between two pressing elements with a scale and electric coils adhered to the external faces of the pressing plates for maintaining the temperature of the fluid.

1 Claim, 5 Drawing Sheets

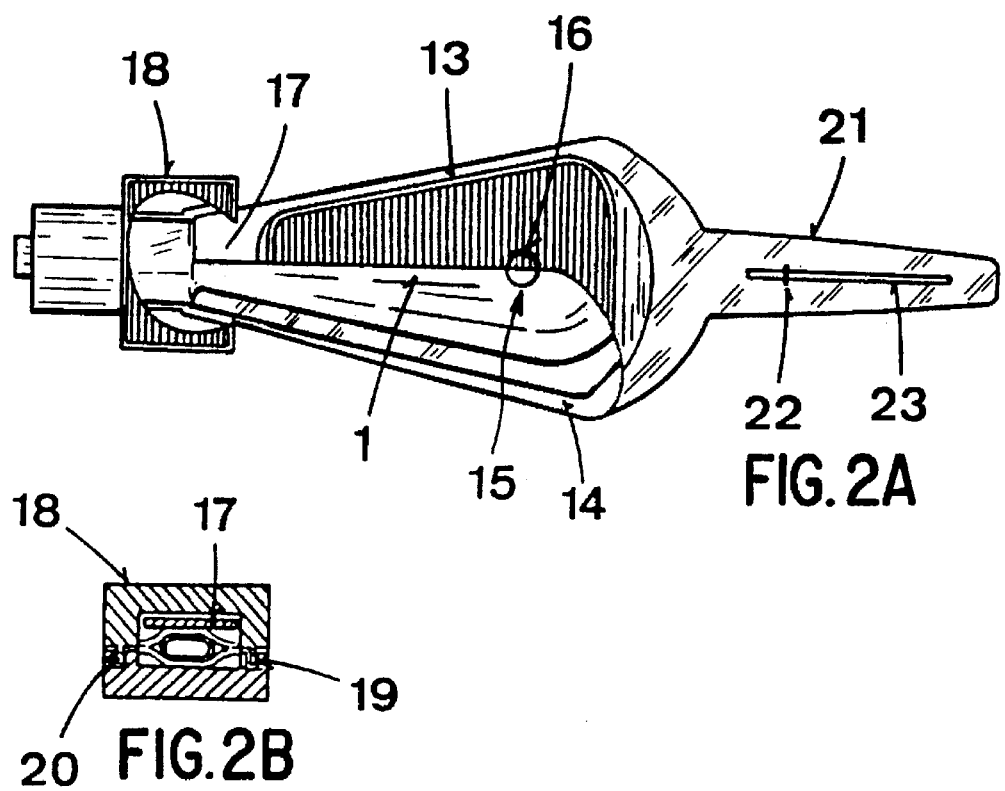
FIG. 2A
FIG. 2B
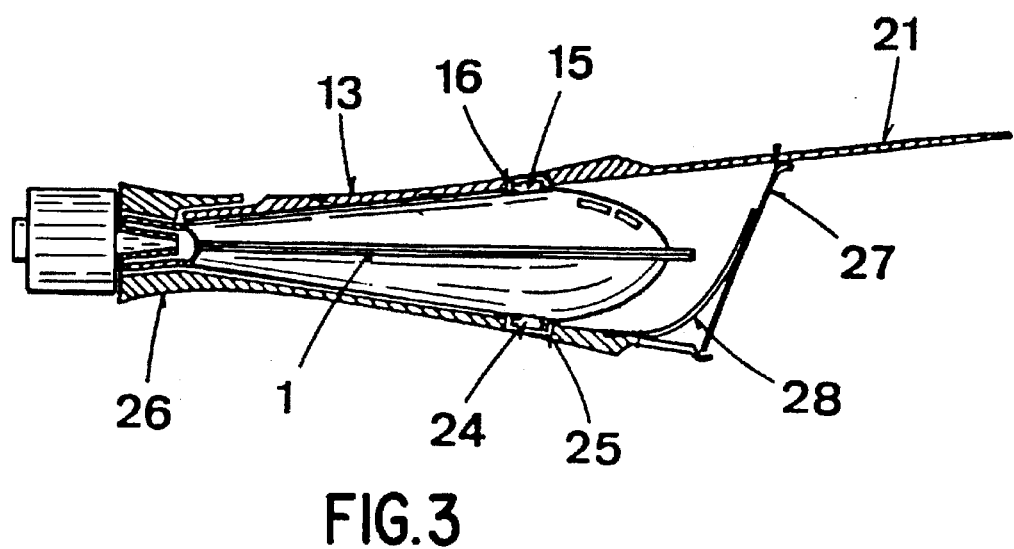
FIG. 3

5,624,407

MEDICATION INJECTING DEVICE AND ACCESSORIES THEREFOR

BACKGROUND OF THE INVENTION

1. Field of the Invention

The present invention refers to a device intended to inject, into humans and animals, solutions for therapeutic or diagnostic purposes. The device already contains the fluid for injection, and is ready for use. The device is disposable, thereby eliminating the need for conventional glass vials, bottles or ordinary syringes.

2. Discussion of the Related Prior Art

Presently, injectable solutions, including pharmaceuticals and contrast media, are available in glass vials, transferred, at the time of administration, to glass or plastic syringes. Syringes already containing contrast media and some pharmaceuticals, ready for use, are also available. Another available device is the pressure injection pistol, usually for vaccines administration through the skin.

Conventional syringes present many recognized disadvantages, as the need to fill the syringe from a separate vial, an uncomfortable and time consuming process, including the risk of contamination and, in many cases, the plunger can be difficult, to manipulate, requiring, in many situations, high pressures on the plunger, as in the use of high viscosity media; in other cases, the volume is to be high, requiring long plungers difficult to operate. In this regard, it has been developed a pre-filled syringe for contrast media with volumes ranging from 50 to 100 ml with a plunger too long to be comfortably operated by practitioners. In addition, pre-filled syringes, including those with therapeutic fluids, have to be manufactured under expensive and too rigid standards to avoid the risk of leakages and contamination. In the case of infusion protocols, a bottle or a bag containing the solution to be administered must be connected to the infusion tubing, by insertion of the tubing spike through the stopper in the bottle or to the connection in a bag requiring some dexterity, being also uncomfortable. Presently, many automated devices to drive conventional syringes are also available, requiring, however, the use of tubings, presenting high cost and usage limited to selected places.

Many attempts have been made to provide alternative devices to the conventional syringes and related fluid administration devices, to overcome their disadvantages.

One type of approach has been to provide an injector system with a pre-filled collapsible reservoir with precisely measured amounts of medication. These devices have flexible walls, so that the contents can be discharged by compressing or squeezing them.

Devices of this type are exemplified in the following U.S. Pat. Nos.:

| U.S. Pat. No. | Patentee |
| --- | --- |
| 789,093 | Dean |
| 1,222,814 | Storz |
| 2,618,263 | Lakso, et al. |
| 3,099,264 | Hubbard |
| 3,114,369 | Hall |
| 4,013,073 | Cunningham |
| 4,018,222 | McAleer et al. |
| 4,130,117 | Van Eck |
| 4,475,906 | Holzner |
| 4,581,021 | Landau et al. |

-continued

| U.S. Pat. No. | Patentee |
| --- | --- |
| 4,955,871 | Thomas |
| 5,261,881 | Riner |

While the above listed prior art devices avoid, in varying degrees, the aforementioned problems associated with plunger-type syringes, they did not find widespread application due to several reasons, as, for example, difficulties in self-injection situations, specially for the physically feeble or diabetics, some present the inability to be used with disposable needles or connector tubings, and in devices provided with needle some mechanism must be included to prevent fluid escape during storage before use, and in the majority of devices of these types, their structural principles are associated with complexity for manufacturing and cost. Another problem with some devices of the type considered is the type of plastic material of the container presenting a tenency to return to its original shape, known as memory, when the applied pressure is relaxed causing introduction of air or tissue aspiration.

Otherwise, regarding the plunger-type syringes, there are situations in which large number of injections have to be performed, as in hospitals, emergency suites and mass vaccination procedures, over a short period of time, when it is virtually impossible to avoid the risk of contamination due to reuse or the many necessary steps for preparation.

Another problem of many such proposed devices is that the fluid container is conceived to be pressed directly by fingers, causing the risk of fluctuations in the injection rate, oscillations of the device, with potential increased trauma to vessel or tissue.

As a result, there has been a need for safer, easier to operate, lower costs medication administration systems, including the low dose, high dose with pressure and infusion devices.

Aiming to present an easier to use and more cost effective alternative to conventional systems, and other devices as those in the above listed patents, it has been developed the present medication injection device and its accessories, seeking to overcome most of disadvantages of prior art devices, wherein the preferred embodiment comprises a squeezable fluid container made, preferably, by two films of a neutral, flexible, pressure resistant and autoclavable plastic material, heat-sealed at the edges, attached to a luer-lock connection, the fluid being propelled, in the small volumes injector, by a pressure applied by fingers, on both sides of the container, on a pair of rigid plastic plates, in this way better distributing the force on the surface, resulting in a stable, ready and easier to use and comfortable to medical practitioners, the same being with large volumes pressure injections deice and even with the infusion package.

Although the invention has been described and detailed according to the preferred embodiment and the concretions here inserted, many modifications and variants can be made on the same, according to the appended claims.

BRIEF DESCRIPTION OF THE DRAWINGS

FIGS. 2A–2B show a partially cutaway view of a preferred embodiment of the present invention, with FIG. 2B showing an end cutaway view;

FIG. 3 shows a sectional view of the device;

DETAILED DESCRIPTION OF THE PREFERRED EMBODIMENT

Figure 1A:
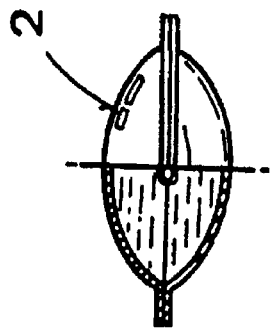
FIGS. 1A–1D show a preferred embodiment of the present invention with FIGS. 1A, 1B and 1C being sectional views of portions of the device shown in FIG. 1D.
Figure 1D:
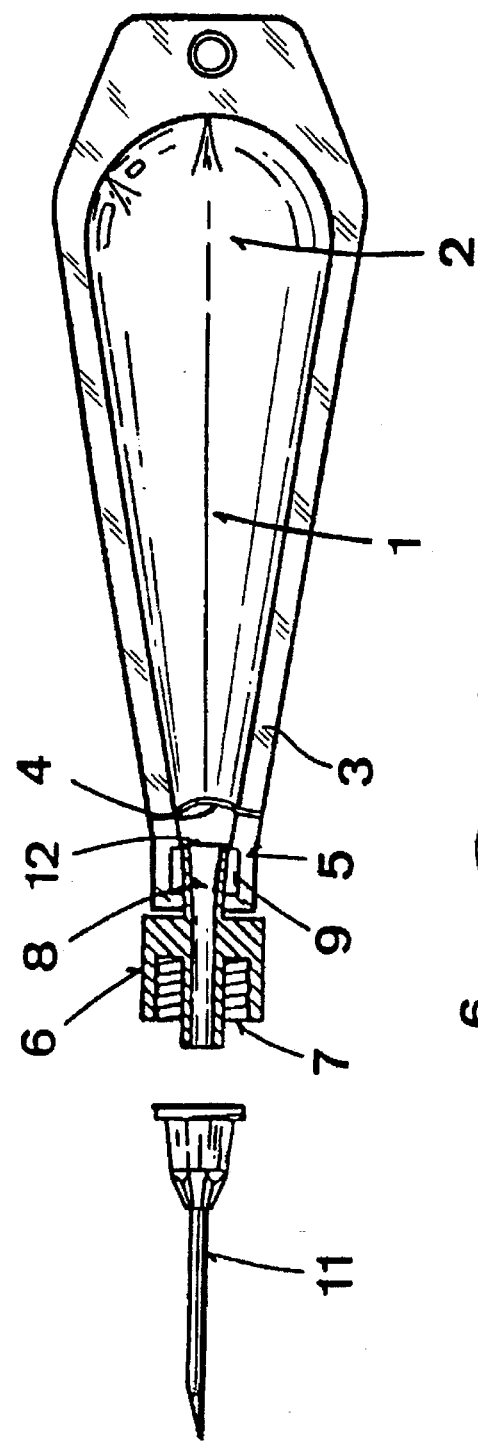
Figure 1B:
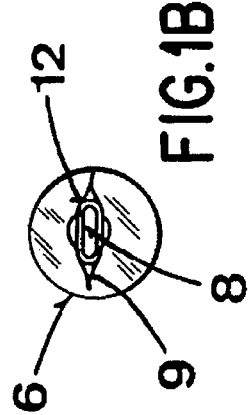
Figure 1C:
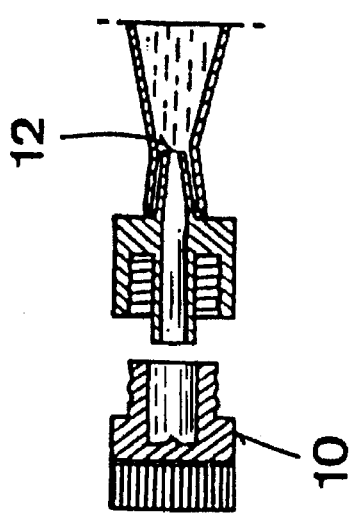

The invention can be better understood with the detailed description of the attached schedules, being:

FIGS. 1A–D illustrate the basic element of the new device, being constituted by the main body of the recipient (1) containing the injectable solution, formed by molding or, preferably, by heat sealing of two plastic films, with a conical shape in an upper view, and oval in a transversal cut-off (cut-AA-) at its larger volume portion (2), whose wall (3) is made, of neutral plastic material, not reacting with the fluid for injection, flexible, pressure resistant, preferably non elastic, or a little elastic for some applications, with a Teflon inner coating (4) as needed, separating the fluid and the wall, increasing safety. At its tapered extremity (5) the recipient (1) is fixed, e.g., by heat sealing, to the terminal element (6) containing the fitting connection luer-lock (7), and the tubular section (8) with the wing (9) to be fixed to the inner face of the tapered wall (5), with the tubular section (8) having its proximal end (12) (cut-BB-) preferably vertically depressed and laterally enlarged to conform to the container (1) depression at the time of fluid ejection. The external cover (10) (cut-CC-) protects and maintains the fluid sterility before use. At the luer-lock (7), the standard needle (11) is fitted.

FIGS. 2A and B illustrate an upper view of the injecting device with accessories for injection of small volumes of fluid, in which it can be observed the recipient (1) installed between two pressing plates (13) upper and (14) lower, fixed to the external surface of the said recipient (1) that contains, at its upper external surface, the tappet (15) fitted in the orifice (16) of the upper pressing plate (13), tapered, with its narrowed end (17) fitted under the upper catcher (18), (cut-DD-), with the fitting pins (19) and (20) that maintain the fixing of the upper and lower catchers. In the figure, it is also shown the scale (21) at the opposite end of the upper pressing plate (13), with the indicator (22) that moves in the slot (23).

FIG. 3 illustrates a lateral cut-off view of the injecting device with accessories to inject small volumes of fluid the fluid container (1) placed between the upper (13) and lower (14) pressing plates, where it can be noted the tappets (15) and (24) respectively in the upper and lower external surfaces of the recipient (1), are fitted in the orifices (16) and (25) in the upper and lower pressing plates. It can also be noted that the lower catcher (26) is preferably, part of the lower pressing plate (14). Between the scale portion (21) of the upper plate (13) and the extremity of the lower plate (14) the arm (27) is placed connected to the foil (28) acting as a spring producing a slight force on the plates (13) and (14), in an approaching way to prevent air suction after needle adaption.

Figure 4:
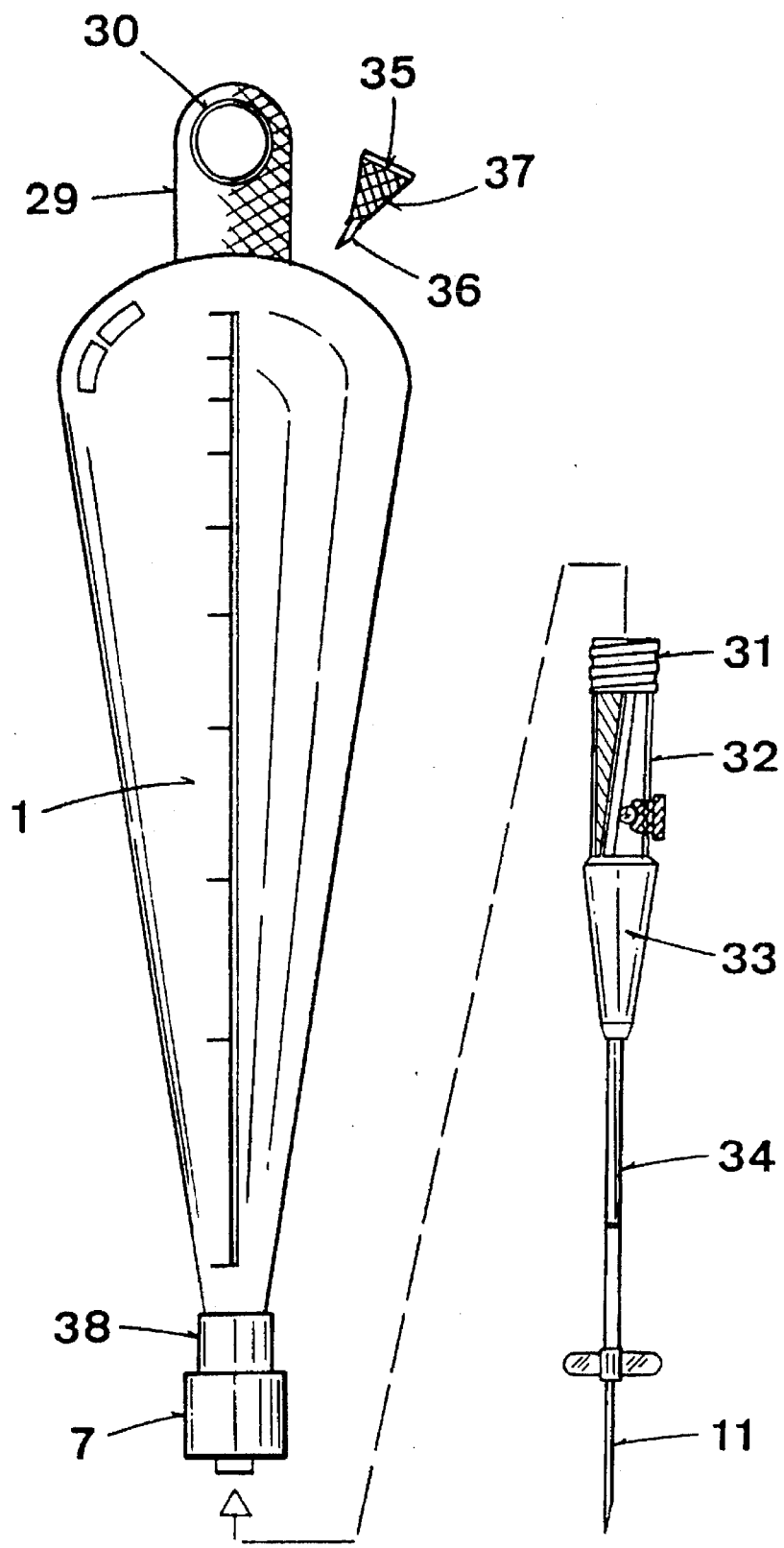
FIG. 4 shows the recipient used in the device.

FIG. 4 shows the recipient (1) of the injecting device, with a suggested shape for large volumes to be administered by infusion or biphasic methods, containing at its larger volume portion (2), the support (29) with the orifice (30) for hanging up. In this administration method, to the luer-lock connection (7) is fixed, preferably , to the terminal (31), fixed to the valve (32) for flow control, placed at the upper part of the dropping chamber (33), and to this, is fixed the tubing (34) up to the needle (11). Completing the device it is showed the air filter set (35), containing the needle (36) to be inserted in the flexible recipient (1) and the container (37). The luerlock (7) set fixing to the container (1) is reinforced by a metal ring (38).

Figure 5:
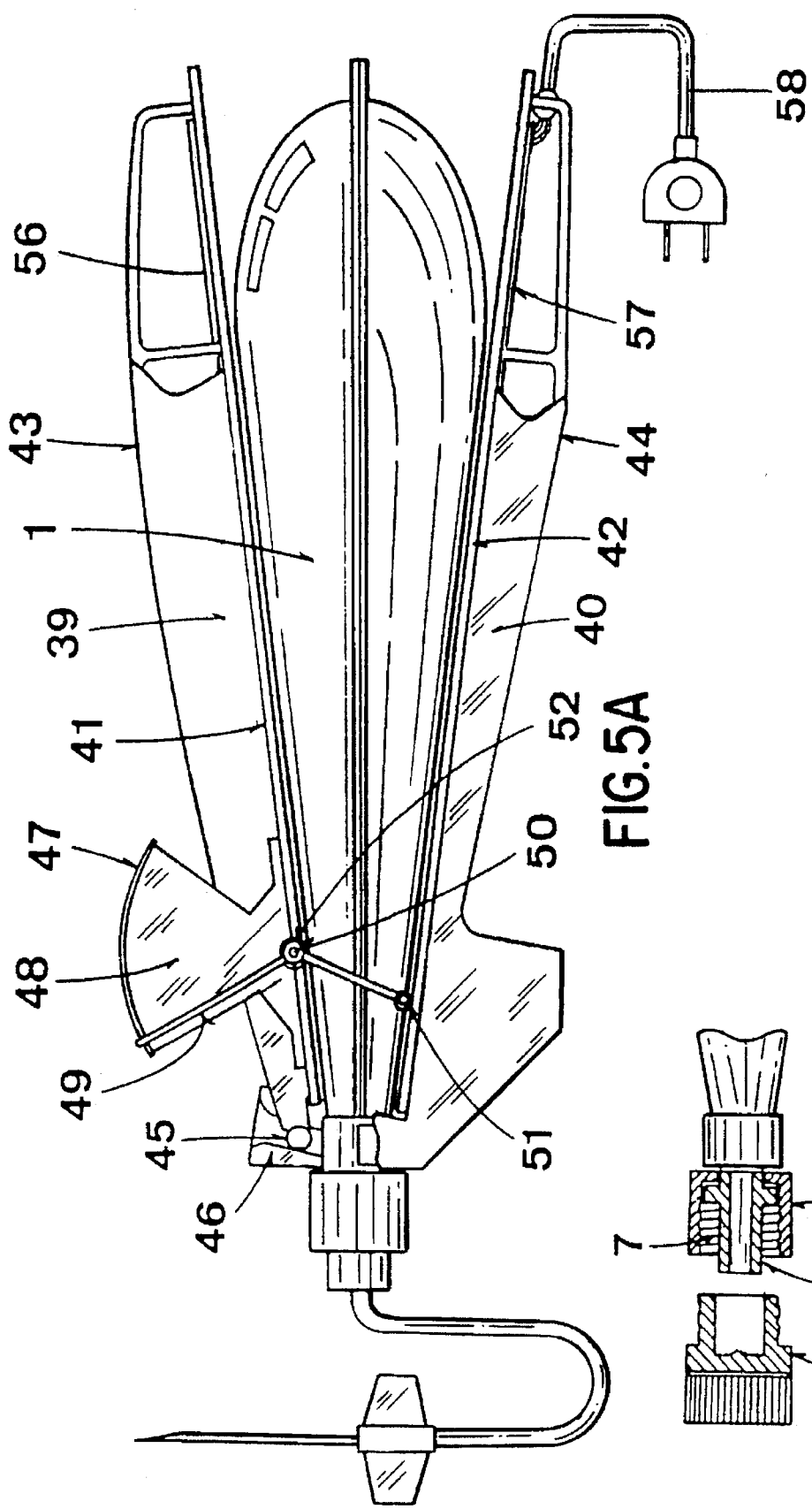
FIG. 5 shows a lateral view of the recipient.

FIGS. 5A and B illustrate a lateral view of the basic flexible recipient (1) of the new device, with a suggested shape for large volumes injection, by bolus, requiring higher pressures, employing the hands instead of fingers, placed between two pressing elements (39) upper and (40) lower, that can be actuated with one of the hands. In the figure, it is observed that the recipient (1) is positioned between the plates (41) and (42), glued to the ergometric elements (43) and (44), whose set compose the elements (39) and (40). In its upper portion, it is observed that the upper element (30) contains the pin (45) inserted in the guide (46), also with a fixing function. The upper pressing element (39) contains, yet, the scale set (47) for indication of the injected volume, containing the body (48) fixed to the upper plate (41). Completing the set there is the angled hand (49) attached at its lower extremity, to the bearing (51) in contact with the lower plate (42). At its angled portion, the hand rotates around the pin (50), containing the return spring (52). The luer-lock (7) contains (cut-EE-), in the case of the large volumes recipient (1) the semi-free external ring (53), able to rotate freely, with the cover (54) to keep the air-tightness and sterility of the content, externally threaded and with an internal tubing in intimal contact with the tip tube (55). Optionally, the fluid can be kept at body temperature of 37° C., by means of electric coils (56) and (57), plane and thin, respectivelly adhered to the external faces of the pressing plates (41) and (42), receiving electric power by the wire (58).

Figure 6:
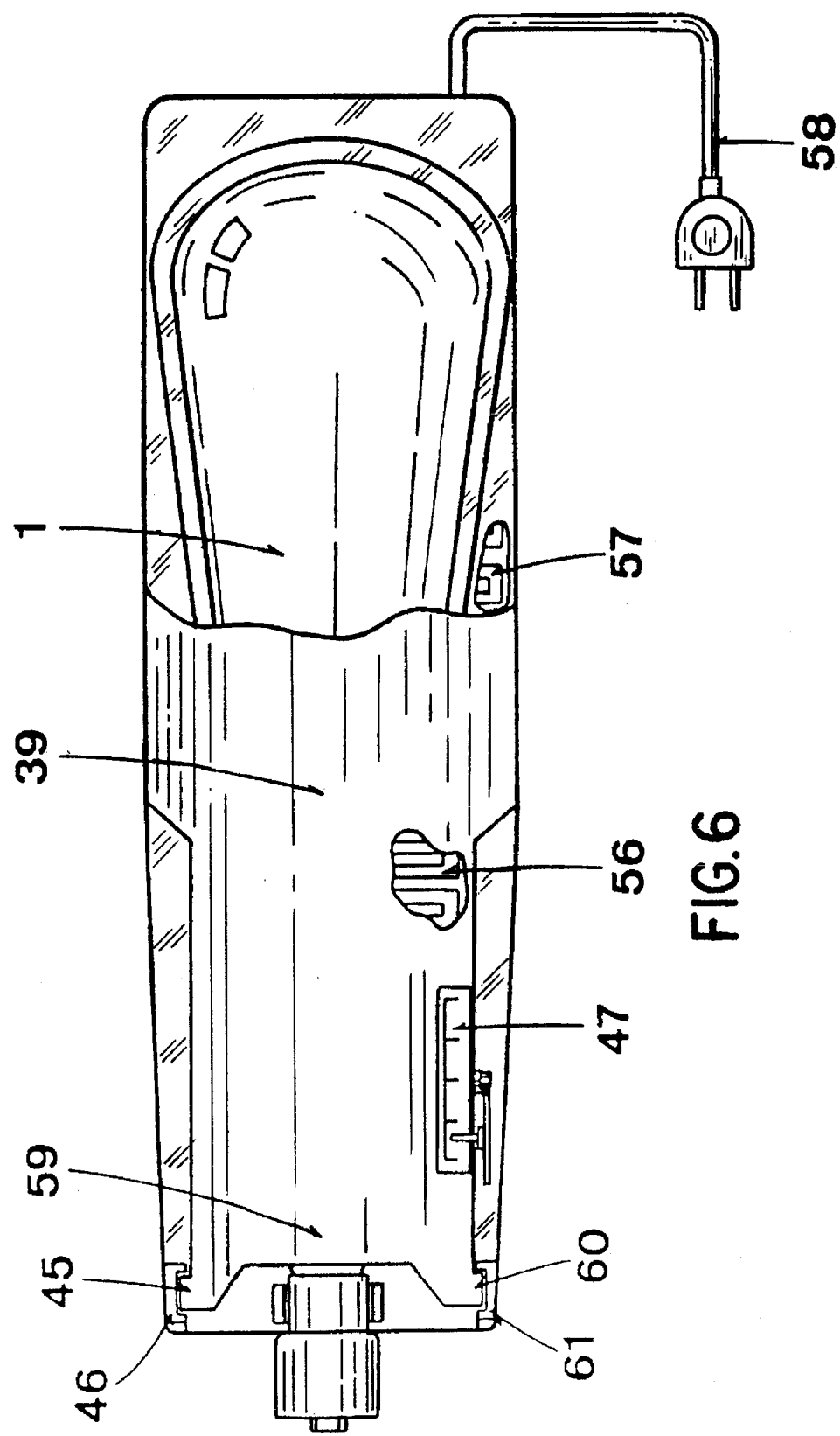
FIG. 6 shows an upper view of the device.

FIG. 6 illustrate an upper view of the device for injection of large volumes of fluid, in which the upper pressing element (39) has an anterior crotched extremity (59), containing, at each side, the pins (45) and (60), inserted in the guides (46) and (61), part of the inferior element (40) The scale mechanism (47) completes the set, indicating the injected volume. The plane and thin coils (56) and (57), respectivelly adhered to the internal faces of the pressing plates (41) and (42), permit keeping, optionally, the temperature of 37° C., by means of the electric power feeding by the wire (58).

I claim:

1. A medication injecting device comprising:

a main recipient containing a fluid for injection, said recipient having distal and proximal ends; and a terminal element having distal and proximal ends heat sealed at its proximal end to said distal end of said recipient, said terminal element having a fitting connection male luer-lock for receiving a conventional hypodermic needle and having a tubular section with a reinforcement wing, said terminal element proximal end being preferably tapered along the longitudinal main axis and enlarged at the transversal plane;

a hypodermic needle;

a flow control valve with an integral dropping chamber said flow control valve having a female luer-lock and being coupled to said male luer-lock via said female leur-lock; and tubing, said tubing having first and second ends wherein said tubing first end is connected to said needle and said tubing second end is connected to said flow control valve dropping chamber.

* * * * *